United States Patent
Cheng et al.

(10) Patent No.: US 7,928,384 B2
(45) Date of Patent: Apr. 19, 2011

(54) LOCALIZED STATIC CHARGE DISTRIBUTION PRECISION MEASUREMENT METHOD AND DEVICE

(75) Inventors: Zhaohui Cheng, Tokyo (JP); Tasuku Yano, Kokubunji (JP); Seiko Omori, Kokubunji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 141 days.

(21) Appl. No.: 12/222,577

(22) Filed: Aug. 12, 2008

(65) Prior Publication Data

US 2009/0057557 A1  Mar. 5, 2009

(30) Foreign Application Priority Data

Aug. 29, 2007  (JP) .................................. 2007-222020

(51) Int. Cl.
*G01N 23/00* (2006.01)
(52) U.S. Cl. ......... 250/310; 250/306; 250/307; 250/311
(58) Field of Classification Search .................. 250/306, 250/307, 310, 311
See application file for complete search history.

(56) References Cited

U.S. PATENT DOCUMENTS

| | | | | |
|---|---|---|---|---|
| 6,521,891 B1 * | 2/2003 | Dotan et al. | ................... | 250/310 |
| 6,653,631 B2 * | 11/2003 | Nishimura | ........................ | 850/1 |
| 6,667,476 B2 * | 12/2003 | Todokoro et al. | ................. | 850/9 |
| 6,828,571 B1 * | 12/2004 | McCord et al. | ............. | 250/492.2 |
| 2002/0179851 A1 * | 12/2002 | Sato et al. | ................... | 250/491.1 |
| 2004/0124364 A1 * | 7/2004 | Sato et al. | ................. | 250/396 R |
| 2007/0040118 A1 * | 2/2007 | Cheng et al. | ................... | 250/310 |
| 2007/0221845 A1 * | 9/2007 | Komuro et al. | .................. | 250/310 |
| 2008/0302963 A1 * | 12/2008 | Nakasuji et al. | .............. | 250/310 |
| 2009/0272899 A1 * | 11/2009 | Yamazaki et al. | ............. | 250/307 |
| 2010/0006755 A1 * | 1/2010 | Sato et al. | ..................... | 250/307 |

* cited by examiner

*Primary Examiner* — Robert Kim
*Assistant Examiner* — Michael Maskell
(74) *Attorney, Agent, or Firm* — Stites & Harbison PLLC; Juan Carlos A. Marquez, Esq.

(57) ABSTRACT

A charged particle beam device including a function for measuring localized static charges on a sample. A primary charged particle beam scans a sample positioned in a mirror state to acquire an image. The acquired image may be an image of the sample or may be an image of a structural component in the charged particle optical system. The acquired image is compared with a standard sample image and the localized static charge is measured.

8 Claims, 12 Drawing Sheets

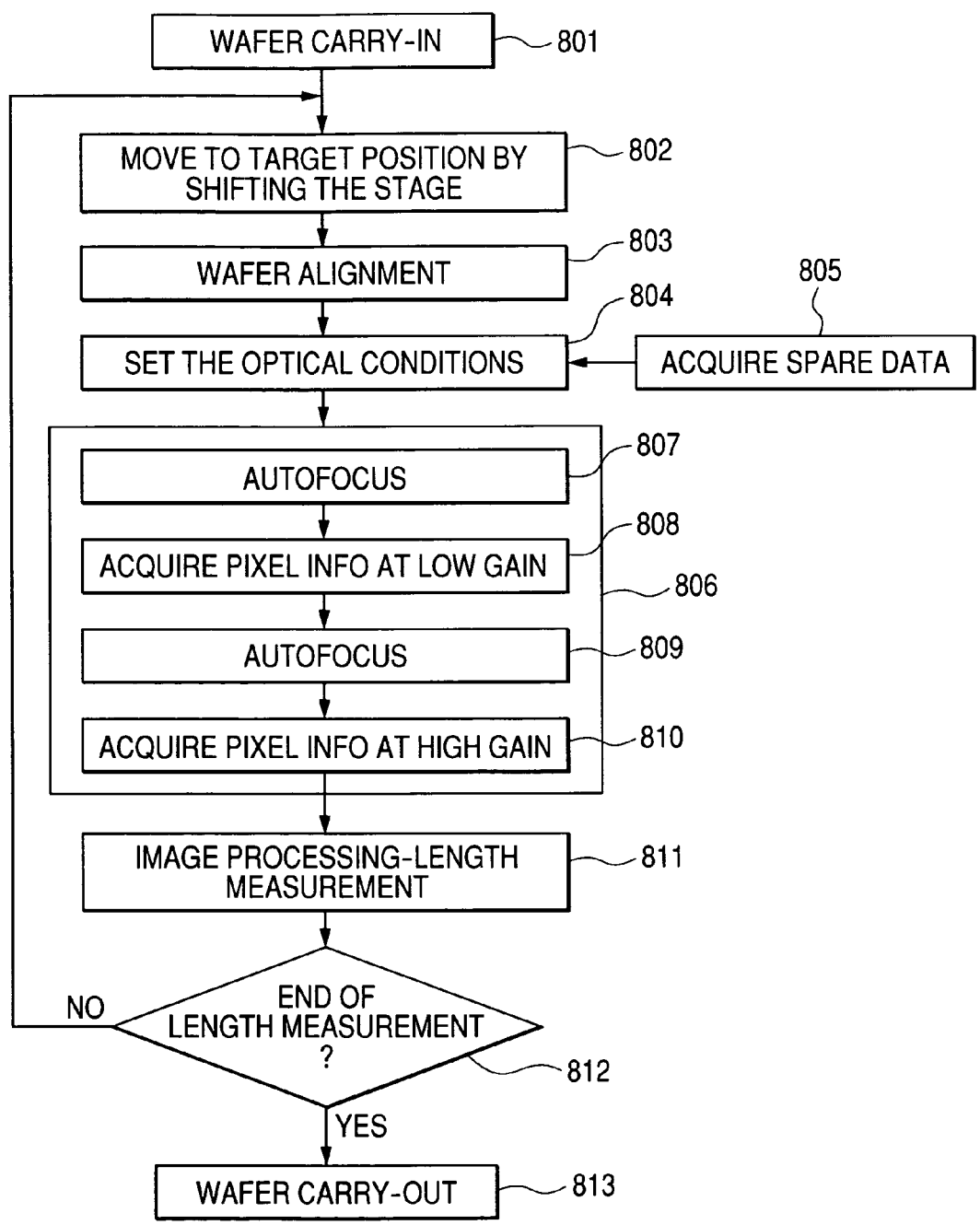

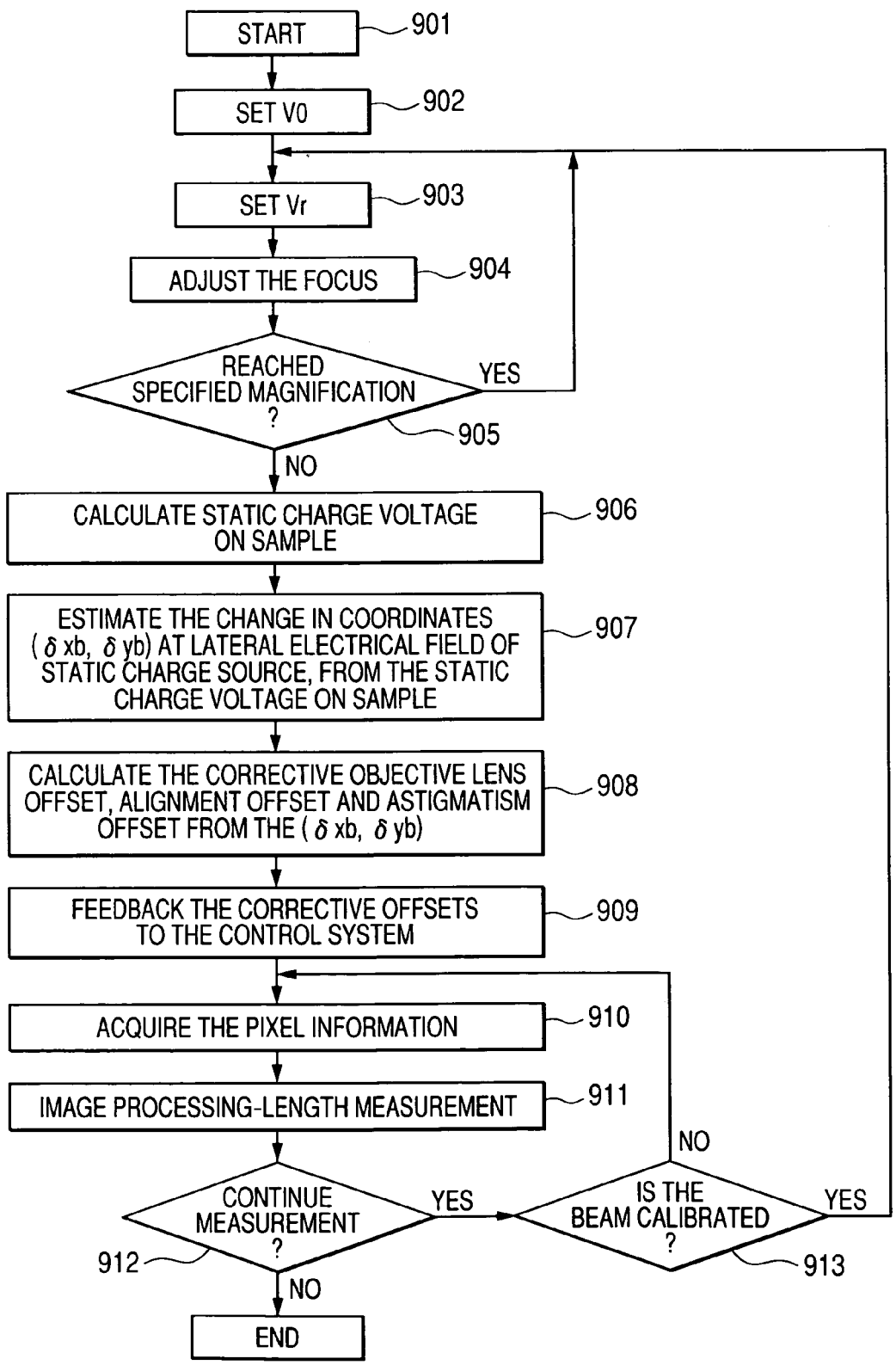

FIG. 10A

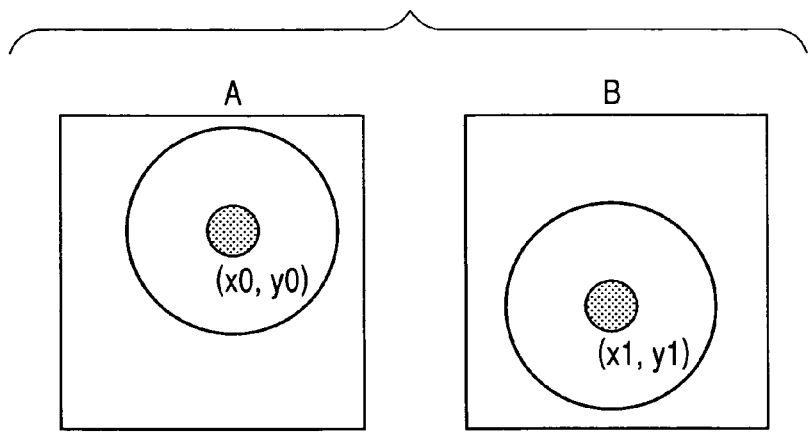

FIG. 10B

| SHIFT QUANTITY | ASTIGMATISM CORRECTION QUANTITY | ALIGNMENT CORRECTION QUANTITY | OBJECTIVE LENS SETTING CORRECTION QUANTITY |
|---|---|---|---|
| (0, 0) | 0 | 0 | 0 |
| ($\delta xb1, \delta yb1$) | ($\delta ib1', \delta vb1'$) | ($\delta ib1'', \delta vb1''$) | $\delta ib1'''$ |
| ($\delta xb2, \delta yb2$) | ($\delta ib2', \delta vb2'$) | ($\delta ib2'', \delta vb2''$) | $\delta ib2'''$ |
| ... | ... | ... | ... |
| ($\delta xbn, \delta ybn$) | ($\delta ibn', \delta vbn'$) | ($\delta ibn'', \delta vbn''$) | $\delta ibn'''$ |

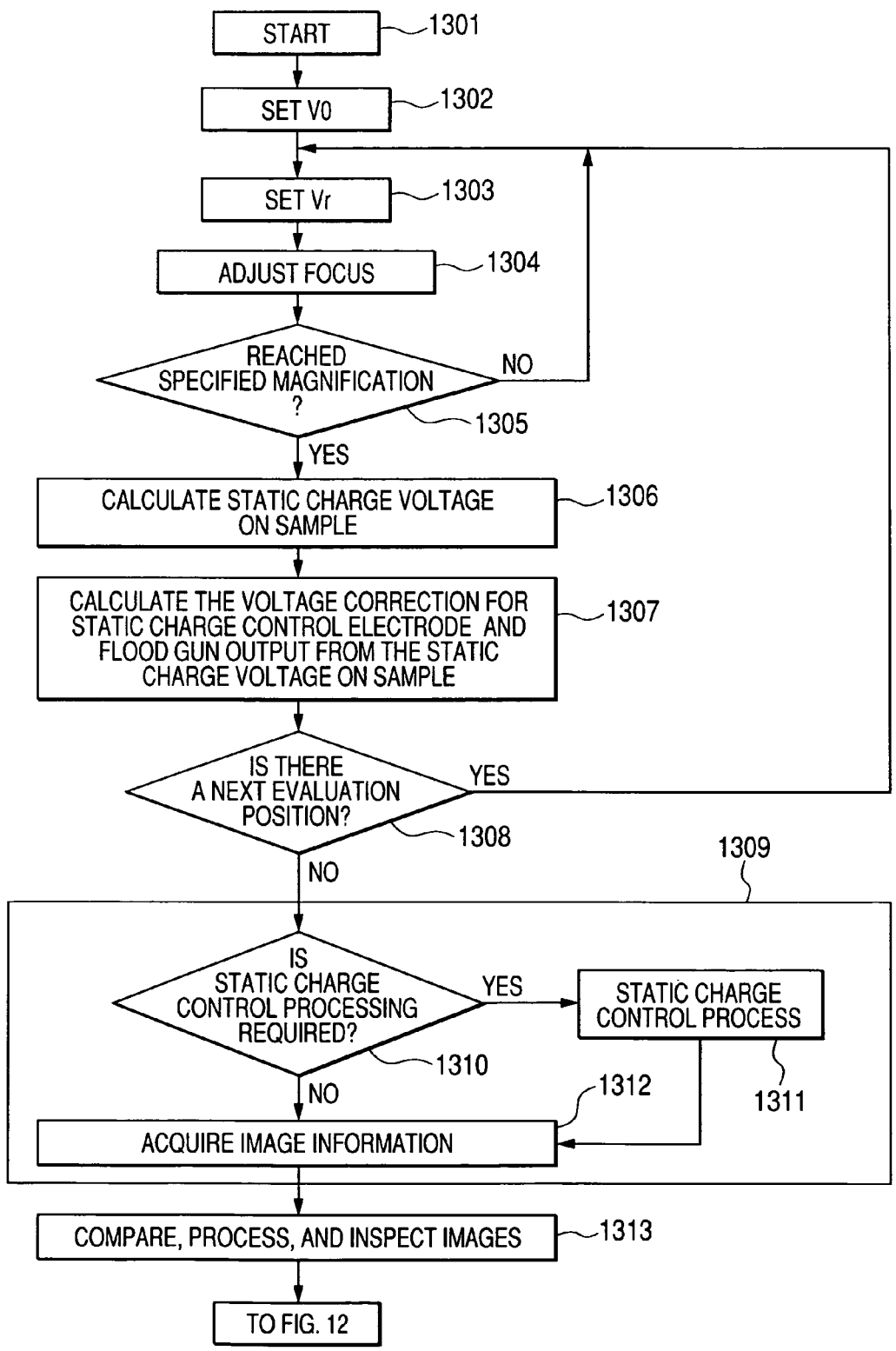

LOCALIZED STATIC CHARGE DISTRIBUTION PRECISION MEASUREMENT METHOD AND DEVICE

CLAIM OF PRIORITY

The present application claims priority from Japanese patent application JP 2007-222020 filed on Aug. 29, 2007, the content of which is hereby incorporated by reference into this application.

FIELD OF THE INVENTION

This invention relates to technology for scanning and measuring a sample such as a semiconductor substrate or liquid crystal substrate, or a substrate or chip formed with a tiny circuit pattern; and relates in particular to a scanning and measurement device for scanning and measuring a sample material based on secondary electron or reflected electron distribution data acquired after scanning the material with a charged particle beam.

BACKGROUND OF THE INVENTION

In devices such as scanning electron beam devices and ion beam devices that scan and measure by irradiating samples with a charged particle beam the problem of irradiation from the primary charged particles causing static charges has long been a serious problem.

When a sample containing insulation material such as a sample containing a wiring pattern formed on an interlayer dielectric film or semiconductor substrate coated with resist is irradiated by an electron beam, that sample becomes statically charged and voltage potential of that static charge causing problems such as bending the primary charged particle beam track, focusing errors and astigmatisms. When these types of phenomena occur, making accurate inspections and measurements is impossible because secondary electron or reflected electron distribution data cannot be obtained that accurately reflects the material distribution and surface contours of the sample. This problem becomes worse as the size of the inspection or measurement target becomes smaller, such as the size of the semiconductor wiring (layer) width or the liquid crystal transistor.

The technology in JP-A-Hei10(1998)-125271 discloses an adjusting unit that adjusts the value of the retarding voltage applied to the sample to offset the static charge, and suppress fluctuations in the quality the scanning electron image obtained in this way. The technology in JP-A-2001-236915 discloses a technology for calculating a static charge map of the material surface, and optimizing the incident energy of the irradiating electron beam according to the static charge voltage from the position where the primary charged particle beam is irradiated, and adjusting the focus of the primary charged particle beam. The technology in WO03007330 discloses a method for measuring localized voltages on the surface of the sample by utilizing an energy filter to acquire the S curve of the secondary electrons. The value measured as the localized static charge voltage is fed back to a deflected signal setting of a scanning deflector to change the image magnification by adjusting the intensity of the deflected signal, and eliminate effects from the localized static charge. In the invention disclosed in WO03007330, there are two types of static charges. One static charge type is a broad region charge and the other type is a localized charge. The broad region charge greatly affects the focus of the charged particle beam and the localized charge greatly affects the magnification of the charged particle beam. These charges must be isolated for measurement.

The invention in JP-A-2003-202217 on the other hand, discloses technology for irradiating a planar beam onto a sample applied with a voltage potential nearly equal the accelerating energy of the charged electron beam, and focusing the charged particle beam planar-reflected from the sample in this state to examine the sample.

SUMMARY OF THE INVENTION

The inventions described in patent documents 1 through 3 are all technology for measuring the quantity of the static charge, and then adjusting the device conditions based on those measurement results, however the charged particle beam must irradiate the sample in order to measure the static charge quantity. The invention described in JP-A-Hei10 (1998)-125271 for example estimates the charge-up voltage of the sample based on the static charge of the primary electron beam that is irradiated. The invention described in JP-A-2001-236915 estimates the surface voltage of the sample based on a video signal acquired from irradiating the primary electron beam onto the sample. Moreover, the invention described in WO03007330 estimates the static charge voltage by acquiring an S curve from the energy filter but in order to acquire the S curve the secondary electrons must be detected. If the charged particle beam reaches the sample then that beam irradiation induces a secondary static charge by irradiating the sample surface so that measuring the static charge prior to irradiating the sample with the beam is impossible.

Whereupon one object of this invention is to provide a method for estimating the localized voltage or voltage gradient of the sample caused by a localized static charge, more accurately than the related art while suppressing the inducing of a secondary static charge due to irradiation by the charged particle beam.

Advances in research revealed that localized static charges affect not only the magnification but also effect the operation of the charged particle optics system in the form of astigmatisms and axial deviations, etc. Whereupon another object of the present invention is to provide a method for compensating effect that localized static charges exert on the charged particle optical system and a charged particle beam device that operates under the operating conditions of that method.

In this invention, the voltage applied to the primary charged particle beam is adjusted to form a state (Hereafter called the mirror reflection state) where the primary charged particle beam does not reach the sample surface, and the localized voltage on the sample surface estimated by detecting and analyzing the returned primary charged particle beam. The primary charged particle beam does not reach the sample placed in a mirror state so an accurate surface voltage value can be obtained without inducing a secondary static charge.

Localized static charge voltages on the sample cause the arrival position of the primary charged particle beam to shift from the correct position on the sample. Therefore, the amount of compensation for the charged particle optical system is found in advance according to the amount of deviation, and during actual operation of the charged particle optical system, the amount of compensation is found from the estimated localized static charge voltage value and is fed back to operate the charged particle optical system. The effect rendered by the static charge is alleviated in this way.

The estimated value for the localized voltage or the amount of compensation applicable obtained from the estimated value is preferably used to set the astigmatism compensation unit.

This invention achieves a localized voltage measurement method for sample surfaces where the induced secondary static charge is lower than in the related art. Moreover, the invention provides a charged particle beam device where the effect of the localized static charge is lower than in the related art.

BRIEF DESCRIPTION OF THE DRAWINGS

FIG. 8 is a flow chart showing the entire operation of the critical-dimension SEM of the first embodiment;

FIG. 9 is a flow chart showing the operation for measuring the localized static charge voltage by mirror electron detection;

FIG. 10 is drawings showing an example of a typical mirror image and an example of a calibration table;

FIG. 13 is a flow chart of the operation for generating a static charge control map and a focus map from the detected mirror electrons.

DETAILED DESCRIPTION OF THE RELATED ART

First Embodiment

In this embodiment, the principle of how the localized static charge occurs is first described followed by a description on estimating the voltage caused by the applicable localized static charge.

Figure 1A:
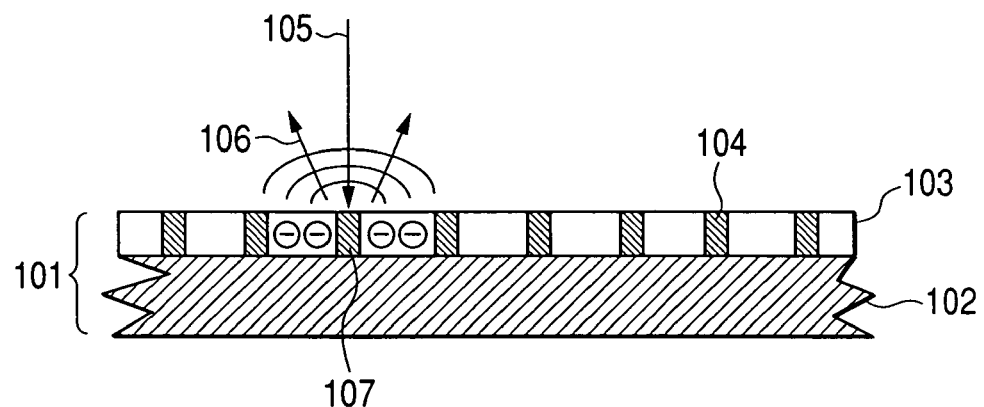
FIG. 1 is diagrams showing the principle for emitting a lateral electrical field due to localized static charges.

FIG. 1 is drawings showing the principle of how localized static charges occur and its effects. A sample 101 shown in FIG. 1A is formed from a conductor section 104 and an insulator section 103 on a substrate 102. When a charged particle beam 105 is irradiated onto the sample 101, then secondary electrons 106 are discharged from the arrival position 107 of charged particle beam 105. When secondary electrons are emitted, then the secondary electrons return to or separate from the sample according to the potential on the sample surface so that an imbalance occurs in the positive and negative charges at the arrival position 107 of the charged particle beam. If the charged particle beam is irradiated onto the conductor piece position then the charge imbalance is canceled out by the charge movement but if there is an insulator piece at the arrival (irradiating) position then charge movement tends not to occur so that the surface of the sample becomes positively or a negatively charged by a static charge.

Figure 1B:
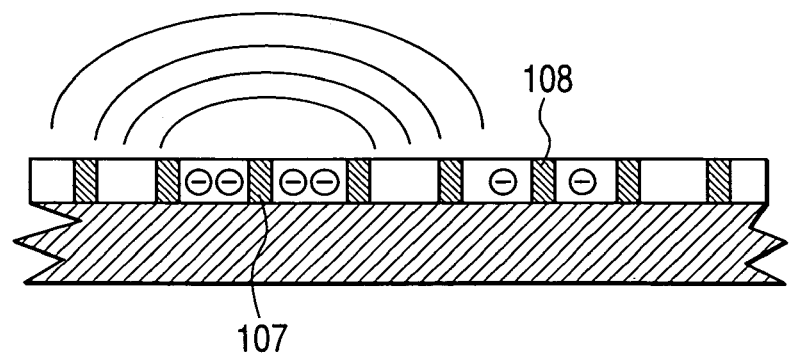
Figure 1C:
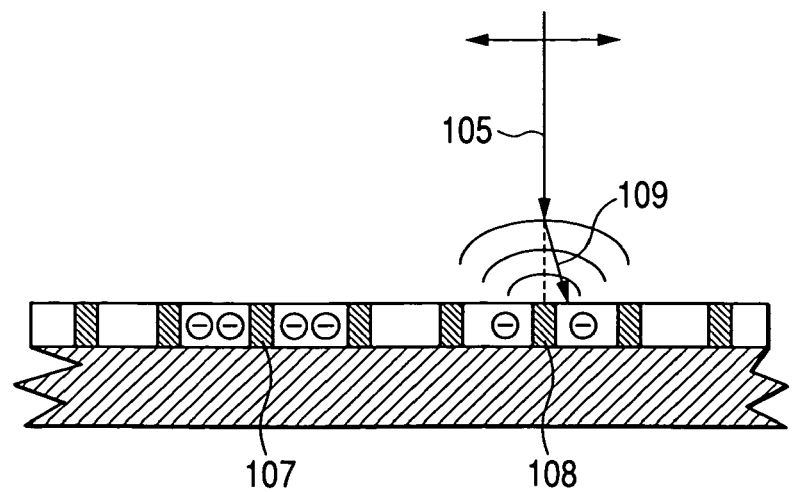

When a particular location on the sample surface becomes statically charged, a voltage distribution forms at the center of the static charge point, and this voltage distribution statically charges the periphery once again. FIG. 1B shows the state where a secondary static charge is formed at a position near the initial static charge position 107. When the charged particle beam is irradiated on the secondary static charge position 108 as shown in FIG. 1C, a new voltage distribution, forms at the secondary static charge position 108 which causes the charged particle beam to bend as shown by the track 109, or the lens affect brought about by the voltage distribution causes astigmatisms, etc. These types of secondary static charges occur in a range from a few nanometers to several hundred micrometers from the initial static charge position 107.

In currently used charged particle beam devices and in particular when adjusting and focusing (retarding focus) the retarding voltage potential, the charged particle beam is irradiated on a position slightly separated from the target observation position (actual charged particle beam irradiating position) and the value for compensating the retarding voltage is set by acquiring the secondary electron signal. A position where the focus can be retained with the range of the image shift from the actual observation position is usually selected as the charged particle beam irradiation position utilized for the retarding focus. This selection serves to prevent changes in the irradiation position due to stage movement. The current state of scanning deflector equipment allows an image shift in a range of about 100 micrometers at most. Irradiating the charged particle beam on a position where the secondary electrons exert no effect is impossible. When the image shift range is too large, the effect of the axial astigmatism causes distortion of the primary charged particle beam itself. Therefore, technology is needed that is capable measuring the static charge on the initial static charge position while suppressing a secondary static charge.

Figure 2A:
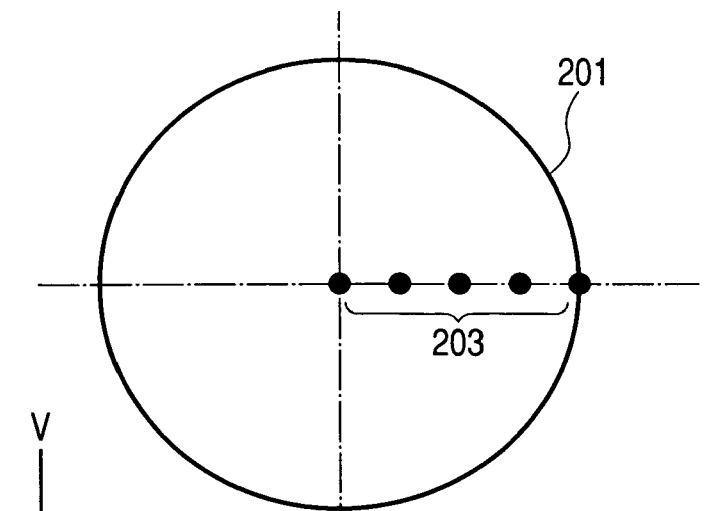
FIG. 2A is a diagram showing the static charge model of a semiconductor wafer.
Figure 2B:
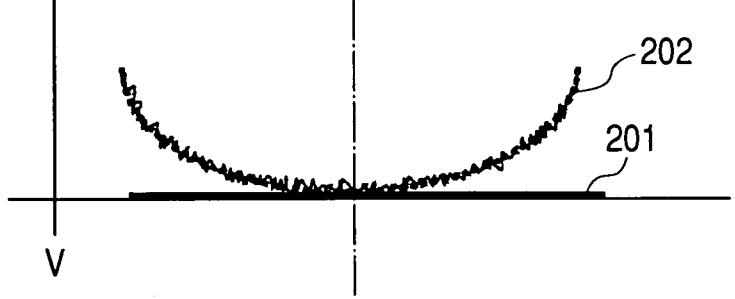
FIG. 2B is a diagram showing the static charge model of a semiconductor wafer.

The actual static charge on the sample is described based on a semiconductor wafer static charge model. FIG. 2A is an upper view of the semiconductor wafer. FIG. 2B is a diagram showing the static charge voltage formed on the applicable wafer. As shown in FIG. 2B a voltage distribution 202 is formed across the entire surface of the wafer 201. A global static charge component 204 fluctuating over the entire surface of the wafer and a voltage component 205 fluctuating on a localized section overlap on this voltage distribution 202. Though there is no academic definition at present, in this embodiment, the global static charge is defined as the component conveyed across the entire surface of the sample in the fluctuating period of the voltage distribution, or is the component where the order of the voltage fluctuating period fluctuates per the extent of the sample length (e.g. ½, ¹⁄₁₀ and so on of wafer diameter). The local static charge on the other hand can be defined as the voltage component fluctuating over a range drastically smaller than the global static charge. The fluctuating period of the voltage distribution for example is the order of the approximate range that can be scanned by the charged particle beam, or the order of the range that the image shift can be deflected, or the approximate size of the chip or die. The local static charge fluctuates for a drastically shorter period than the global static charge and if that fluctuating component can be isolated from the global discharge then that component can be defined as the local static charge.

Figure 2C:
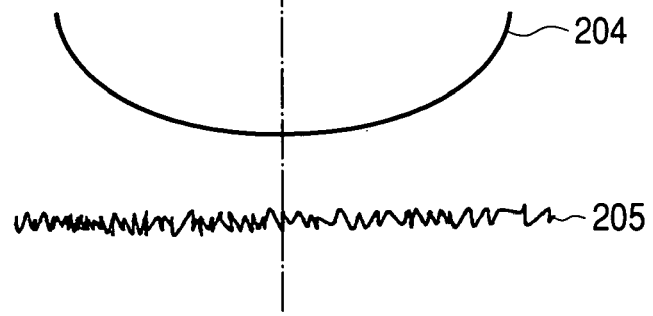
FIG. 2C a diagram showing the static charge model of a semiconductor wafer.

As shown in FIG. 2C, the voltage distribution of the global static charge 204 is very symmetrical. Therefore, if measuring the surface voltage after setting multiple measurement points 203 on the wafer 201 then the voltage distribution of the global static charge 204 can be estimated from the actual values acquired from measuring the surface voltage. However, the voltage distribution 205 caused by the local static charge overlaps onto the actual static charge distribution 202, so setting an operation compensation value for the charged particle optical system such as the retarding focus requires extracting information from the local static charge voltage distribution as well as the global static charge.

The principle of the mirror reflection state, and the actual technique for measuring the voltage potential of the local static charge by focusing the primary charged electron beam into a specified pattern in the mirror reflection state, and detecting the charged particles emitted from the specified pattern is described next.

Figure 3:
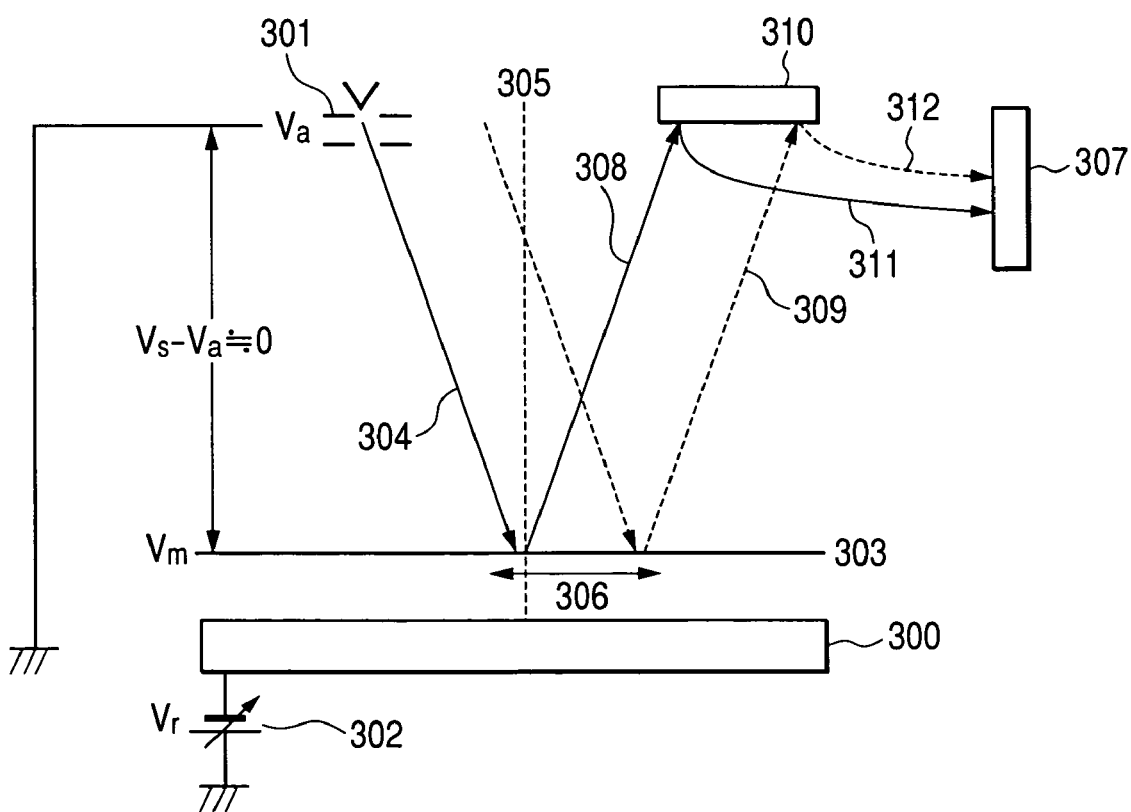
FIG. 3 is a drawing showing the principle of the mirror state.

FIG. 3 is a drawing for describing the mirror state. A primary charged particle beam for an accelerating voltage $V_a$ is irradiated towards the sample 300 from the charged particle source 301. A retarding voltage $V_r$ of the same polarity as the charged particle beam 304 is applied onto the sample from the power supply supply 302. The charged particle beam 304 accelerated at $V_a$ is decelerated directly in front of the sample by the retarding voltage $V_r$, but when $V_a$ and $V_r$ are approximately the same size, the charged particle beam 304 does not reach the sample and is reflected by a specified reflecting surface 303. The position of the reflecting surface 303 can be adjusted by changing the size of the retarding voltage $V_r$. The higher the retarding voltage, the farther the reflecting surface 303 is positioned from the sample surface.

The charged particles 308 reflected from the reflecting surface 303 are reflected at an angle identical to the input angle (input angle of primary charged particles 304 versus the tangent 305 of the sample surface) of the primary charged particle beam 304. When the primary charged particle beam 304 scans a specified scanning range 306 in this state, the charged particles 309 moving in parallel with the charged particles 308, strike the specified pattern 310. A detector 307 synchronized with the scanning signal of the primary charged particle beam detects the secondary signals 311, 231 generated by the specified pattern 310 and an image is then formed. The range in which the charged particles are detected by the detector is set by the magnification scale on the path from reflecting surface 303 to specified pattern 310, and the distance from reflecting surface 303 to the detector 310. Restated in other words, the size of the image detected in the mirror reflecting state is determined only by the height of reflecting surface 303 if the magnification scale of the focusing is fixed. Stated conversely, the height of the reflecting surface 303 on the upper section of the sample can be estimated from the size of the image acquired in the mirror state, or in other words, the size of the retarding voltage $V_r$.

The primary charged particle beam 304 actually contains an energy distribution so that not all the charged particles are reflected at the same reflective surface. However if the reflecting surface at which particles are reflected on the average is known, then this is sufficient for estimating the retarding voltage $V_r$. Moreover, besides the primary charged particle beam reflected from the reflecting surface while in the mirror state, a portion of the high energy charged particles reach the sample surface and therefore contain secondary electrons and reflected electrons from the sample. Therefore the following description proceeds based on the fact that besides, containing the so-called mirror-reflected electrons, the secondary particles detected in the mirror reflecting state also contain an extremely small number of secondary electrons and reflected electrons.

Figure 4:
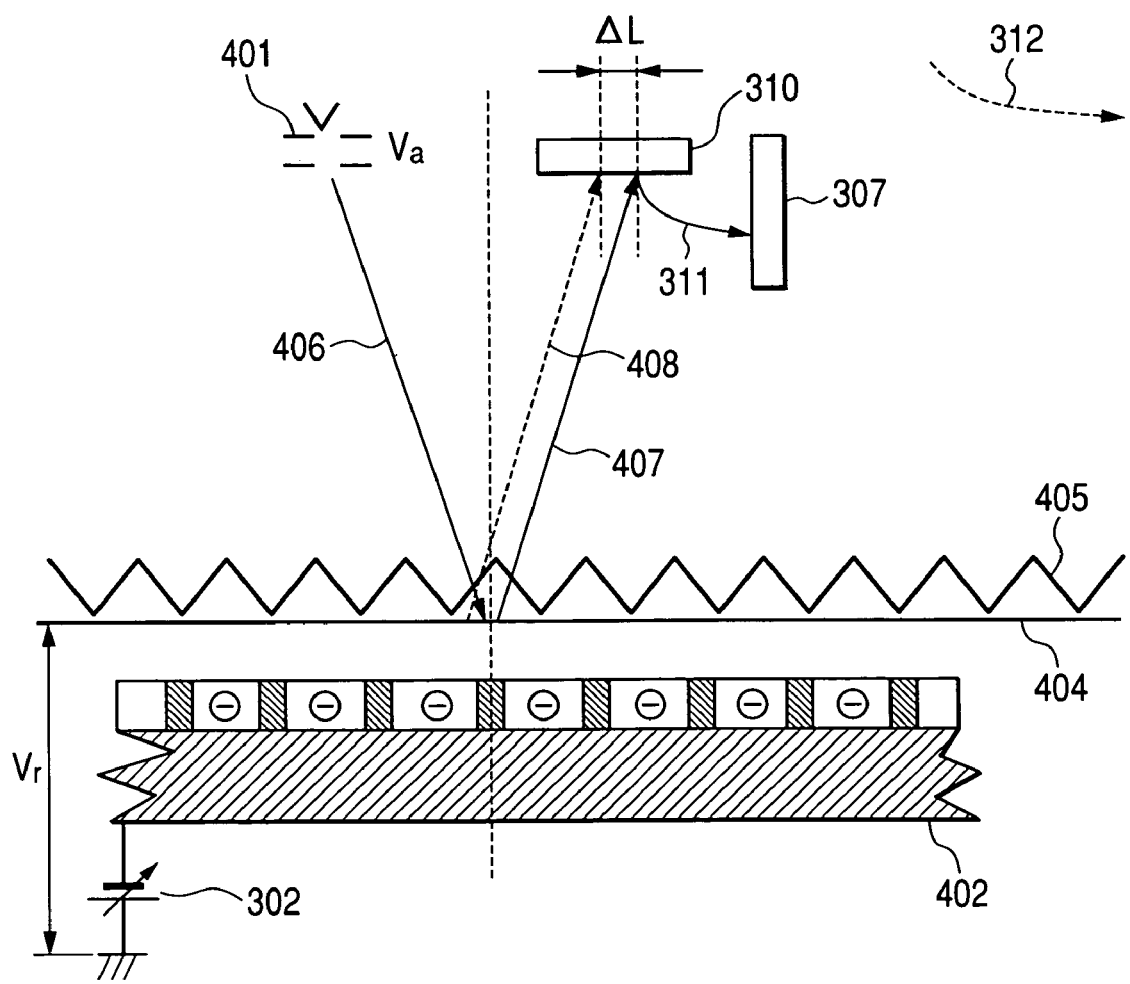
FIG. 4 is a drawing for describing fluctuations in the mirror reflection position due to static charge.

FIG. 4 is a drawing for describing the principle for calculating the localized static charge voltage, by detecting the charged particle beam detected in the mirror reflecting state. Primary charged particles form the accelerating voltage $V_a$ are irradiated onto the charged sample 402 from the charged particle source 401. A retarding voltage $V_r$ is applied to the sample 402 from the retarding power supply 403. A global static charge distribution in fact is overlaid onto the sample 402 as shown in FIG. 2B, and the global static charge distribution at the target irradiation position of the primary charged particle beam 406 is already compensated by the retarding voltage $V_r$. If there is a localized static charge voltage distribution 405, then the primary charged particle beam 406 is reflected by the specified mirror reflecting surface 404 determined by the retarding voltage $V_r$, and the accelerating voltage $V_a$ and the static charge on the sample, and reaches the detector device by way of a path essentially that of the charged particle beam 407 emitted in the mirror state. However, if overlapped by the local static charge voltage distribution 405, then the primary charged particle beam is reflected at a position shifted just by the differential between the mirror reflecting voltage and the localized static charge voltage. The position of the emitted charged particles that reached the specified pattern 3 is in this way made to deviate just by the ΔL compared to when there is no localized static charge voltage distribution. The localized static charge distribution (lateral electrical field distribution) can therefore be estimated by measuring this deviation. For purposes of simplicity, the reflecting surface 404 is formed at a position lower than the voltage distribution of the localized static charge but this reflecting surface 404 may also be positioned in the voltage distribution 405.

In view of the above, the following technique is proposed for quantitatively estimating the localized static charge voltage.

The relation between the retarding voltage and amount of deviation in the image detected in the mirror state is first of all found using a sample with no static charge such as a silicon wafer or metallic substrate with nothing formed on their surface. The amount of deviation in a sample with no static charge is the amount of change in the retarding voltage $V_r$ at the position that the detected primary charged particles irradiate onto the specified pattern. Moreover, the calibration curve for finding the amount of shift due to the lateral electrical field from the localized static charge distribution is also found in advance.

The above described spare data is found, and this time an actual sample, such as a semiconductor wafer on which an insulating film is formed, is placed in a mirror reflecting state, and the primary charged particle beam is scanned at the space on the upper section of the sample. The amount of deviation due to the localized static charge is found from the widening (second dimensional distribution=pattern surface area if image, first dimensional distribution=profile length if profile data) of the specified detected pattern image, and the localized static charge voltage can then be inverse-calculated from the deviation amount.

Figure 5:
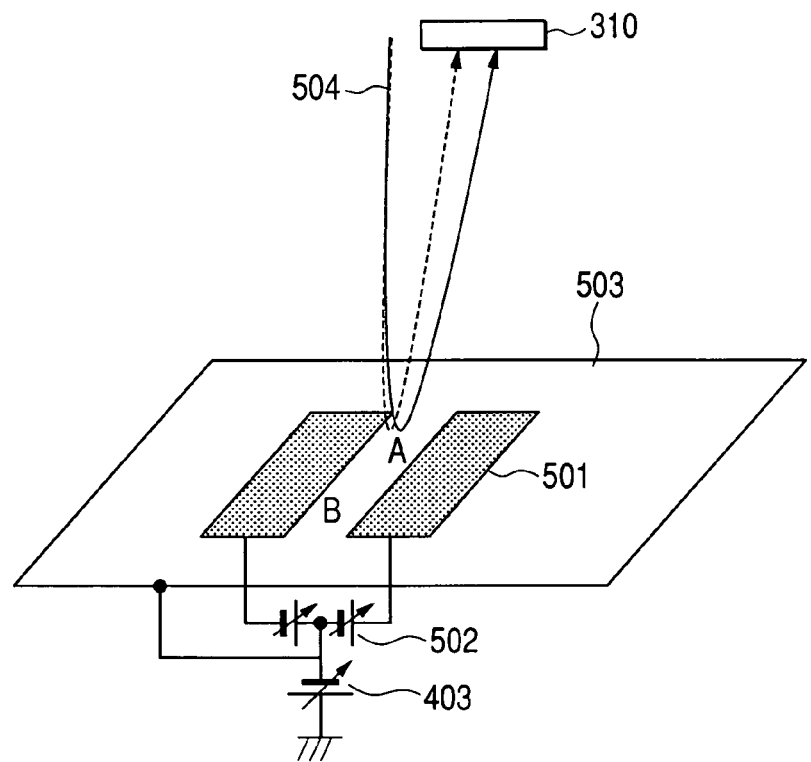
FIG. 5 is a drawing showing the structure of the device for finding the amount of shift due to a localized static charge.

The method for finding the calibration curve in order to calculate the amount of shift in the primary electron beam arrival position due to the lateral electrical field caused by the localized static charge, from the localized static charge voltage is described next. FIG. 5 is a drawing showing the method for finding the applicable calibration curve. An insulated electrode 501 pair enclosing the sample 503 is prepared, and a variable power supply 502 then applies a voltage across the applicable pair of electrodes. A voltage $V_r$ is set at the center position between this electrode pair and a mirror state is set. A charge particle beam 504 at a specified accelerating voltage is irradiated and a measurement made at the irradiation position on the specified pattern 310. Though not shown in the drawing, a secondary electron detector is installed near the charged particle beam 504 arrival position of FIG. 5. Measurements are made at each mirror (reflecting) position, and a database formed. If the extent that the arrival position of the charged particle beam has deviated due to application of a voltage to the electrodes is measured, then the amount of deviation at the arrival position due to the voltage gradient, or in other words the amount of shift caused by the voltage gradient of the localized static charge can be found.

Figure 6A:
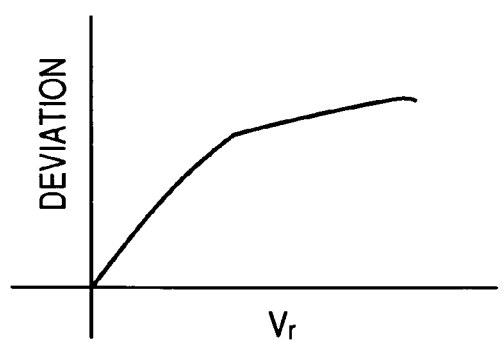
FIG. 6A is a graph showing the amount of deviation versus the retarding voltage.
Figure 6B:
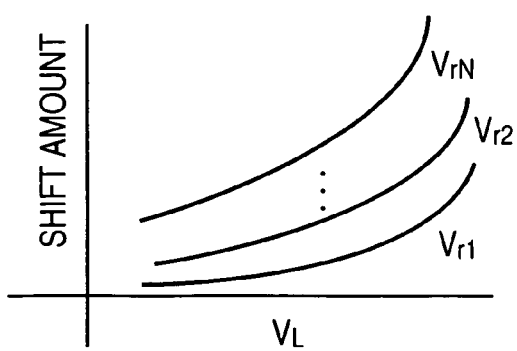
FIG. 6B is a graph showing the calibration curve for the shift quantity and localized static charge voltage.

FIG. 6A is a graph curve showing the shift amount dependency on the retarding voltage $V_r$. FIG. 6B is graph curves showing the dependency of the primary electron beam shift quantity based on the lateral electrical field of the localized static charge voltage found by the method in FIG. 5.

During actual use, finding the compensation amount for localized axial deviations and astigmatisms occurring due to localized static charges is essential rather than value of the localized static charge itself. Devices such as an astigmatism corrector or deflector are therefore placed on the optical axis of the charged particle beam 504, along with the shift quantity, the amount of voltage or current to apply to astigmatism corrector or compensator, or the amount of voltage or current to apply to the deflector in order to cancel out the shift quantity is found. The axial deviations and astigmatisms caused by the localized static charge can in this way be corrected by utilizing the image shift quantity detected in the mirror state.

Second Embodiment

In this embodiment, the structure utilizes a method for calculating the local static charge voltage described for the first embodiment. The critical-dimension (CD) SEM is a device that acquires an SEM image of the specified measurement object and uses image processing to find the distance between two optional points on the image, and that is widely used mainly in the semiconductor device field.

Figure 7:
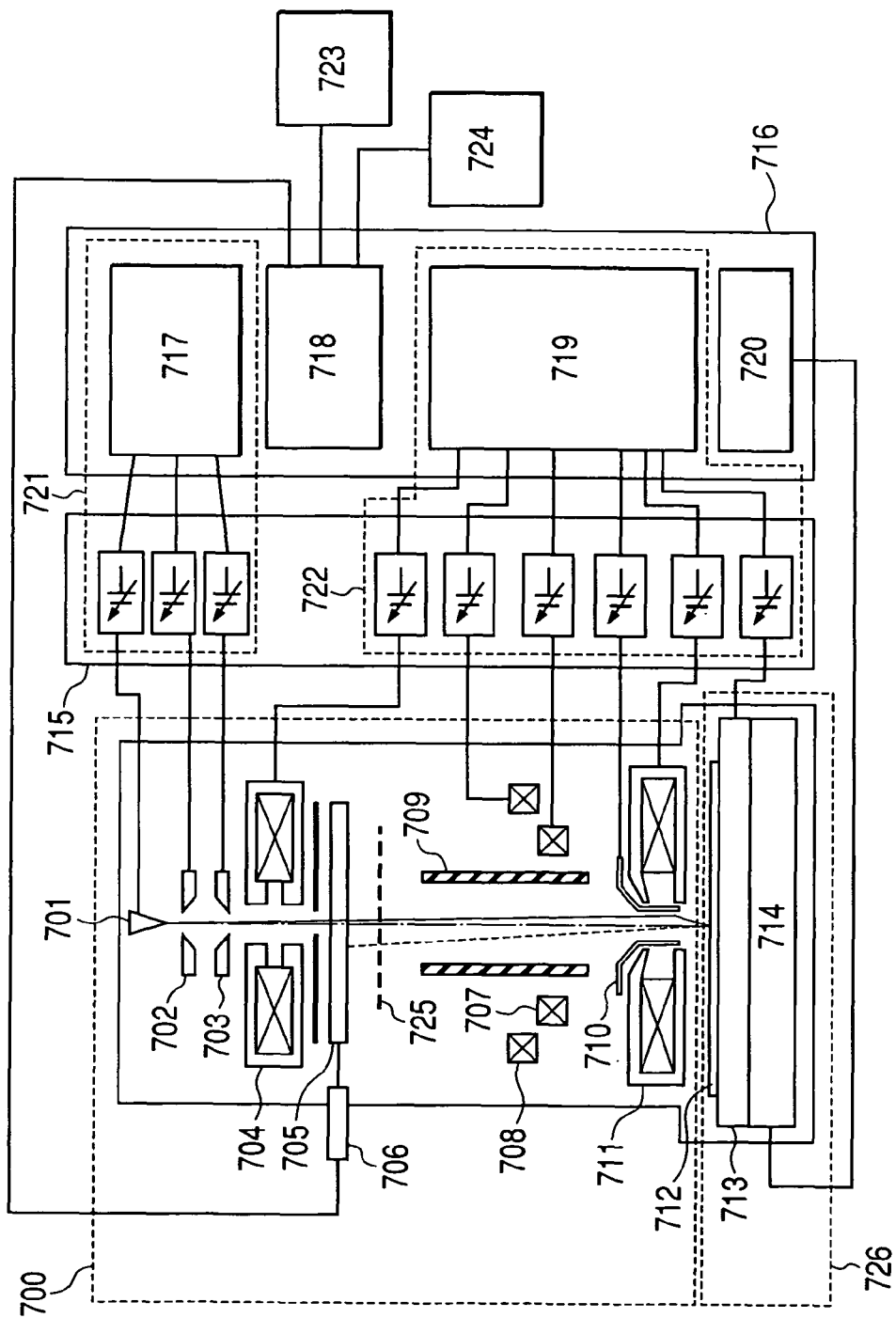
FIG. 7 is a block diagram showing the system structure of the critical-dimension SEM of the first embodiment.

FIG. 7 is a drawing showing the overall structure of the critical-dimension SEM of this embodiment. A brief description of the inspection device of this embodiment is related next. The SEM inspection device includes a sample chamber 726 for storing the sample, an electron optical system 700 including functions for irradiating a primary electron beam onto the sample, detecting the secondary charged particles that are emitted (secondary electrons or reflected electrons or mirror reflected electrons) and outputting the detection results as a signal, a power supply unit 715 containing functions as a cluster of control power supplies for supplying a current or voltage to the drive sections of each component of the sample chamber 726 and electron optical system 700, a control unit 716 for controlling the power supply unit and electron optical system, a length measurement 723 for measuring the length based on detected secondary charged particle signals, and a display screen 724 for displaying images of the secondary charged particle signals and length measurement results.

The electron optical system 700 includes an electron gun made up of an accelerator electrode 703, an electron source 701, and an extractor electrode 702, an electron irradiating system on the lower section of the electron gun, as well as a detection system for secondary charged particles. The electron beam (Shown by the solid line extending downward from electron power supply 701 in FIG. 7. The dotted line indicates the electron beam optical axis) whose electrons are attracted from the electron power supply 701 by applying a voltage across the electron power supply 701 and the extractor electrode 702. The electron beam is accelerated at the same time by applying a negative high voltage to the accelerating electrode 703.

The electron beam system includes a condenser lens 704 and aperture below that condenser lens, a tube electrode 709, a boosting electrode 710, an objective lens 711 for focusing the primary electron beam on the sample, a scanning deflector 707 for scanning the primary electron beam in a specified range on the sample, and an astigmatism corrector 708. The condenser lens 704 and aperture below that condenser lens are installed to adjust the current of the primary electron beam. The tube electrode 709 is grounded, and the tube electrode 709 and the boosting electrode 710 below it generate an electrical field to accelerate the primary electron beam. The primary electron beam accelerated by the boosting electrode 710 passes through the objective lens 711, is decelerated by a retarding voltage $V_r$ (negative voltage potential) applied to the sample stand 713, and reaches the sample surface. The position where the primary electron beams arrive on the sample is deflected by the scanning deflector 707 and secondary charged particles are generated in this way.

The secondary charged particles generated from the sample surface are accelerated in the reverse direction of the primary electron beam by the electrical field formed by the voltage potential of the retarding voltage and the boosting voltage 701. The accelerated secondary charged particles afterwards pass through the energy filter 725 and reach the secondary charged particle detector 705, and a secondary charged particle signal emitted. This secondary charged particle signal is amplified by the preamp 706, and then input to a signal processor circuit in a latter stage. Though some components are redundantly used a components in the primary electron beam system, for purposes of simplicity, the detection system in this embodiment includes a boosting electrode 710, a tubular cylinder 709, an energy filter 725, and a secondary electron detector 705, etc.

A sample stand 713 for mounting the measurement sample 712, and an XY stage 714 for shifting the sample stand along the specified XY directions are installed in the sample chamber 726. A retarding voltage is supplied to the sample stand 713 from the power supply unit 715.

A control unit 716 controls each of the components of the above described electron gun, electron optical system, and detection system. The control unit 716 contains multiple subsystems for controlling each unit in the electron optical system. The control unit 716 for example contains an electron gun control device 717, an electron optical system control device 719, a stage control device 720, and an information processing device 718 for processing the secondary charged particle signals, etc. Each sub-system is linked to each control power supply and includes an electron gun control system 721, and electron optical control system 722. The electron optical system 700 and the sample chamber 726 are each stored in vacuum containers.

The secondary charged particle signal amplified by the preamp 706 is input to the information processor device 718. The information processor device 718 links the signal readout from the secondary charged particle detector 705 with the scan timing of the primary electron beam. The secondary charged particle signal that was input to the information processor device 718 is converted to digital data by AD (analog/digital) conversion and from there onwards, the signal processor within the information processor device 718 executes the digital signal processing. The AD converter is installed as a post stage immediately downstream of the preamp 706, and AD conversion may be implemented immediately after amplification by the preamp 706.

FIG. 8 shows the operation flow of the devices in FIG. 7. The description in this embodiment uses an example where a wiring pattern is formed as the sample object for measurement. Needless to say however, the applicable object for applying the embodiment is not limited to a semiconductor wafer.

The sample is carried into the sample chamber 726 in step 801. The stage is then moved in step 802 to shift the measurement location on the wafer to the primary electron beam irradiation position. Wafer alignment is performed in step 803 by matching the actual coordinates on the wafer with the XYZ coordinate system used by the electron optical control system 722. The primary electron beam optical system irradiation conditions are set in step 804. The operation 805 to read out the spare data as described in the first embodiment is executed at the same time, and the amount of astigmatism compensation and amount of compensation for the retarding voltage are calculated.

The image acquisition step 806 is then performed and the high magnification image acquired for each measurement point on the wafer. Strictly speaking, the image acquisition step 806 is includes the autofocus 807 and low magnification pixel acquisition step 808, and the autofocus 809 and high magnification pixel acquisition step 811. The length measurement step 811 is implemented by image processing after acquiring the pixel information at the measurement points. After measurement of the target points is completed, a decision step 812 is implemented to decide whether or not to end the length measurement. When length measurement of all the measurement points is completed, the operation proceeds to the wafer carry-out step 813, and if there are still points for measurement remaining then the process returns to step 802, and the stage moves to the next measurement position.

The process flow for measuring the localized static charge voltage using the secondary charged particles detected in the mirror state is described next utilizing FIG. 9. The flow shown in FIG. 9 is utilized to describe in detail a portion of the operation executed in the optical condition setup step 804 of FIG. 8.

The step for adjusting the images acquired in the mirror reflecting state is implemented in the initial steps 902-905. When the process flow starts in step 901, the accelerating voltage $V_0$ of the electron gun is set in step 902, and the primary electron beam irradiation conditions are decided. The respective retarding voltage $V_r$ values are next set in step 903. The initially set value $V_r$ here is the default value. A fine adjustment is made in a latter step for obtaining the mirror electrons at the desired magnification and the final value then decided.

In step 904, the primary electron beam is scanned in the mirror state and a fine focus adjustment of the secondary signal image made for the specified pattern. The focus here need not be adjusted by adjusting the objective lens 711 in step 904. The focus may also be adjusted here by using the focus point depth as an optical condition. In this embodiment, the image acquired in the mirror state is an image of the energy filter 725. The energy filter is a metal mesh installed on the optical axis. After the secondary charged particles passes through the energy filter, the secondary charged particle detector 705 detects an unchanged image of the mesh shape. The secondary charged particle detector 705 contains an opening for passing the primary electron beam and so the image actually detected by the secondary charged particle detector 705 is an image synthesizing the captured image of the mesh contour along with the shadow of the secondary electron detector opening.

In step 905 a decision is made on whether the magnification of the image detected in step 904 is the desired size or not. The magnification rate of the secondary charged particles emitted from the sample in the mirror state is changed by the height of the surface reflecting the secondary charged particles or in other words, the retarding voltage. So if the image is not at the desired magnification value then the process flow returns to step 903, and the $V_r$ value is reset. After resetting the $V_r$ value, the spare image is acquired and the focus adjusted in step 904, and a magnification decision made in step 905. If the magnification is the desired value then the process flow proceeds to step 906. If not the desired magnification then the operation is repeated from step 903 to 905. When finished adjusting the magnification, the primary electron beam at the wafer effective voltage potential is irradiated onto the sample and a mirror electron image of the energy filter acquired in step 906. The acquired mirror image is then compared with the mirror image in the spare data called up in step 805 of a sample having no static charge, and the amount of deviation in the image calculated. FIG. 10A shows an example of a mirror image found in step 906, and a reference image (mirror image for a sample with no static charge) found as the spare data. The reference image is shown in A, and the image of the wafer with a static charge acquired in the mirror state is shown in B. The solid line circle is equivalent to the contour of the energy filter, and the black dot in the center section is equivalent to the opening in the secondary electron detector. When there is a static charge, the center coordinates $(x_0, y_0)$ of the reference image opening, can be observed to shift to $(x_1, y_1)$. The differential $(\delta x_b, \delta y_b) = (x_1 - x_0, y_1 - y_0)$ between these two coordinates is equivalent to the deviation amount. The calculated deviation amount is then compared with the calibration curve deviation amount minus the retarding voltage serving as the spare data. The calculating process calculates the actual surface voltage $V_r$ of the wafer that affects the primary electron beam. The localized static charge of the sample surface can in this way be found by calculating the differential $V_r'-V_r$ of the surface voltage and retarding voltage potential applied to the wafer.

Then in step 907, the localized static charge quantity that was found, is next compared with the calibration curve in FIG. 6, and the change in coordinates $(\delta x_b, \delta y_b)$ are found for the primary electron beam arrival position generated by the lateral electrical field. The astigmatism compensation amount, primary electron beam alignment compensation amount, and objective lens compensation amount are then calculated in step 908 from the coordinate change amount $(\delta x_b, \delta y_b)$. Each compensation amount is stored in the information processing device 718 in a format such as a calibration table. FIG. 10B shows an example of the calibration table stored within the information processing device 718. The astigmatism compensation amount and the applied voltage compensation amount for the astigmatism corrector and for the primary electron beam alignment deflector, and the excitation current compensation amount for the objective lens are stored as a pair with the shift amount $(\delta x_b, \delta y_b)$ in the table. A processor inside the information processing device 718 checks the table in FIG. 10B and then calculates each compensation amount. In step 909, these calculated compensation amounts are conveyed to the electron optical system control device 719, and each control power supply controlled by the electron optical control system 722 adjusts the operating voltage and current of each unit in the column based on these conveyed compensation amounts.

When finished adjusting the electron optical system after the above steps, the acquisition step 910 for obtaining pixel information utilized in the actual measurements is executed. This step is the same as the image acquisition step 806 in FIG. 8. This step in fact contains steps such as the high magnification image acquisition step utilized in the measurement and the low magnification image acquisition step for finding the visual field center of the measurement position. The length measurement unit 723 executes the pixel calculation when the pixel information is acquired and measures the length of the measurement position (step 911).

When finished measuring the target position the process proceeds to step 912, and need/no-need decision step is implemented on whether to continue the measurement. A beam calibration need/no-need step 913 is implemented to execute further measurement. The step 802 of FIG. 8 is also executed simultaneously, and the stage moves the next measurement position to the primary electron beam irradiation position. If beam calibration is not needed then the image acquisition step 910 is executed at the next stage movement destination. If the beam calibration is needed again then the operation returns to step 903 and the operation in the steps from 903 to 910 is repeated. If continued measurements are not needed then the measurement is terminated in step 912.

The device described in this embodiment renders an SEM for length (critical dimension) measurement including a function for measuring the localized static charge voltage and whose electron beam irradiation causes extremely little damage to the sample. Moreover an SEM for critical dimension measurement is rendered that is capable of suppressing axial deviation effects from the primary electron beam and astigmatisms caused by a lateral electrical field resulting from the localized static charge. An SEM for critical dimension measurement is in this way achieved whose electron beam irradiation imparts extremely little damage and has excellent length measurement reproducibility.

In this embodiment, the amount of deviation was calculated by utilizing an image of the energy filter. However, the effect of the embodiment is clearly obtained even if an image of another structure contained in the electron optical system such as a reflecting plate of a secondary charged particle, or an image of a specified measurement point formed on the sample is utilized to calculate the amount of deviation. Moreover, the structure of this embodiment is not limited to an SEM for critical dimension measurement and needless to say, is applicable to all manner of devices utilizing electron beams where static charge problems tend to occur such as external inspection devices and review SEM, etc.

Third Embodiment

An example of an SEM type external inspection device is described in this embodiment. An SEM type inspection device is a device for detecting defect points such as electrical flaws and foreign matter by acquiring SEM images of the semiconductor wafer surface where circuit patterns such as wiring and contact holes are formed, and then comparing the acquired images. SEM type inspection devices are widely used on semiconductor device production lines, etc.

Figure 11:
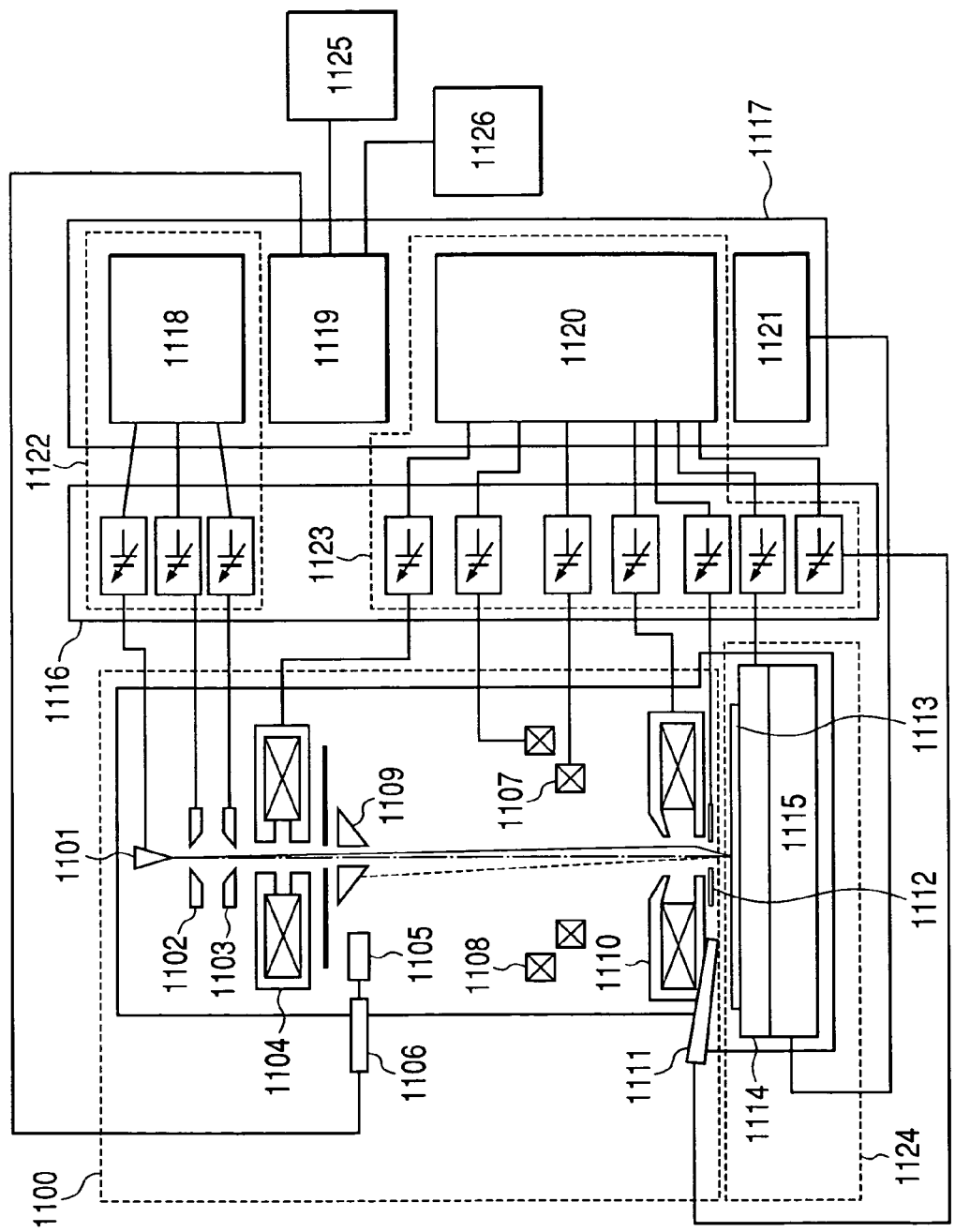
FIG. 11 is a block diagram of the system structure of the SEM external inspection device of the second embodiment.

FIG. 11 is a block diagram showing the system structure of the SEM type inspection device of this embodiment. Many sections of the overall structure are identical to the critical-dimension SEM shown in FIG. 7 so a description of operations and functions is jointly used sections is omitted. The following description uses FIG. 11.

The SEM type inspection device of this embodiment usually contains a sample chamber 1124, an electron optical system 1100, a power supply unit 1116, a control unit 1117, an image processor unit 1125 for detecting the position of defects based on the detected secondary charged particle signals, and a display screen 1126 for displaying an image from the secondary charged particle signal and the image results.

The electron optical system 1100 includes an electron gun containing an electron power supply 1101, an extractor electrode 1102, and an accelerator electrode 1103; and an electron irradiating system for the section below the electron gun, and a system for detecting the secondary charged particles.

The electron beam system includes a condenser lens 1104 and an aperture below that condenser lens, a scanning deflector 1107 for scanning the primary electron beam in a specified range on the sample, and an astigmatism corrector 1108, an objective lens 1110 for converging the primary electron beam on the sample, a flood gun 1111 for irradiating a flood beam (an electron beam that is not converged) onto the primary electron beam irradiation position, and a static charged control electrode 1112 installed in a lower section of the objective lens, etc. A retarding voltage $V_r$ is applied to the sample stand 1114 the same as the device in FIG. 7.

The secondary charged particles emitted from the sample surface strike the reflecting member 1109 and emit secondary particles (also called tertiary charged particles). These g1105, and are detected as secondary charged particle signals. These emitted secondary charged particle signals are amplified by the preamp 1106 and input to the signal processing circuit in a latter stage. In an actual structure, an E×B deflector is installed between the reflected member 1109 and the objective lens 1110 for isolating the primary electron beam and secondary charged particle paths but this makes the structure more complicated and is therefore omitted from the drawing in FIG. 11. Moreover in this embodiment, the detector system includes an E×B deflector, a reflector member 1109, and a secondary electron detector 1105, etc.

The sample chamber 1124 contains a sample stand 1114 where the sample material 1113 is mounted, and an XY stage 1115 for shifting the sample stand in a specified direction along the XY planes. A power supply unit 1116 supplies a retarding voltage to the sample stand 1114.

The control unit 1116 that controls each component of the electron gun, electron optical system, and detection system; contains subsystems such as an electron gun control device 1118, an electron optical control system device 1120, a stage control device 1121 and an information processor device 1119 for processing secondary charged particle signals. Each subsystem is linked to each control power supply, and form an electron gun control system 1122 and an electron optical control system 1123, etc. The electron optical system 1100 and the sample chamber 1124 both include internal vacuum containers.

The SEM type inspection device of this embodiment contains a function to control the static charge voltage in the image acquisition area. This function is implemented by the flood gun 1111 irradiating a flood beam onto the sample while in a state where a specified voltage is applied to the control electrode 1112. The electron optical device 1120 controls the flood beam output, or in other words the flood gun 1111 drive voltage and the voltage applied to the static charge control electrode 1111.

Figure 12:
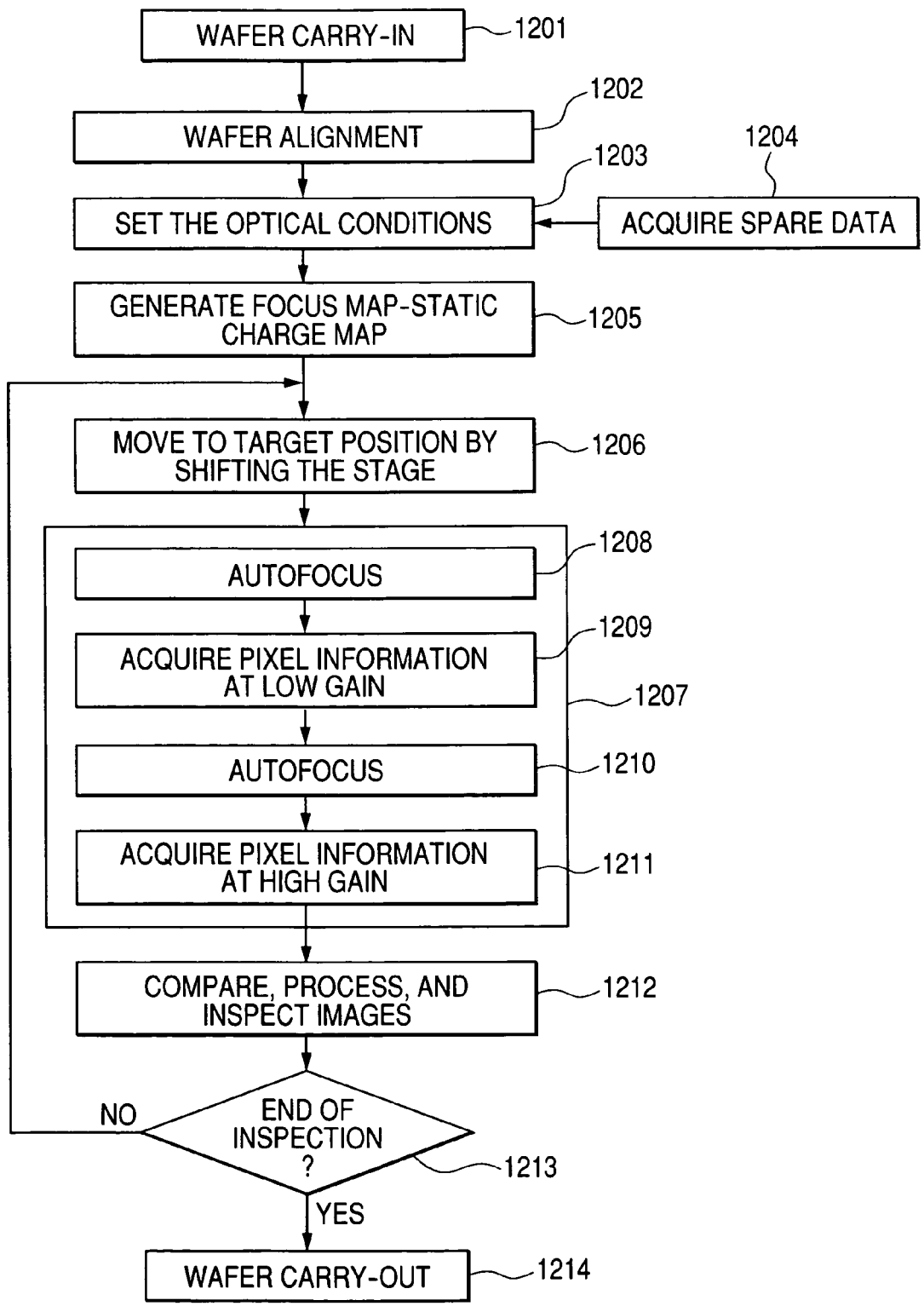
FIG. 12 is a flow chart of the overall operation of the SEM external inspection device of the second embodiment.

The overall operation of the device shown in FIG. 11 is described next. FIG. 12 shows the operation flow of the SEM type inspection device of FIG. 11. In this embodiment, an example utilizing a semiconductor wafer formed with a wiring pattern as the sample object for measurement. However, the sample object for measurement of this embodiment is not limited to a semiconductor wafer.

In step 1201, the sample is carried into the sample chamber 1124. In step 1202, wafer alignment is performed, and the actual coordinates on the wafer are matched with the XYZ coordinates in the electron optical control system 1123. In step 1203, the primary electron beam optical irradiation conditions are set, and image data acquired for generating a focus map and a static charge control map. A spare data read out operation 1204 is executed at this time for calculating the sample surface voltage potential and generating the focus map and static charge control map. The astigmatism compensation amount and retarding voltage compensation amount are calculated at this same time.

The focus map is data where the focus adjustment amount is mapped at each point over the entire surface of the sample. More specifically, the focus map is a data table for storing the excitation current value of the objective lens and retarding voltage value paired with the coordinates on the sample. The static charge control map is a data table for mapping the flood gun drive voltage and the matching voltage applied to the static charge control electrode for the same coordinate as stored in the focus map. Ideally the map preferably contains data for static charge control and focus adjustment control for all points where the inspection is made. However this type of inspection requires too large of an overhead time so usually a focus map and static charge map are made only for specific evaluation points formed at intervals on the sample. The static charge voltage in the specified range on the sample for example might deviate greatly from the predicted voltage distribution of the global static charge due to the localized static charge caused by the quality of the circuit pattern and the type of wafer. If the deviation area is known beforehand, then a static charge control map can be generated for just those types of areas. The number of measurement points can also be increased in those types of areas more than in other areas to generate an effective focus map or static charge control map. The astigmatism compensation amount, primary electron beam alignment compensation amount, and objective lens compensation amount may be calculated the same as in the first embodiment and incorporated into the focus map data.

After generating the focus map and static charge control map, the image data acquisition step 1207 is performed. The image acquisition step 1207 includes an auto focus step 1208 and low magnification pixel information acquisition step 1209, and auto focus step 1210 and high magnification pixel information acquisition step 1211. When the pixel information is acquired for each measurement point, the inspection step 1212 is performed by image comparison processing, and a decision step 1213 also performed to decide whether or not to end the inspection. When inspection of all points is complete, the operation proceeds to the wafer carry-out step 1214, and if the next inspection position is still remaining then the operation returns to step 1206 and from there onwards each step from step 1206 to 1213 is repeated.

The optical condition setting step 1203 and the focus map—static charge control map step 1205 of FIG. 12 are described in detail while referring to FIG. 13.

The steps 1301-1305 are steps for adjusting the image quality of the image acquired in the mirror reflection state, and are identical to the first embodiment so a description is omitted here. The SEM inspection device of this embodiment makes the focus adjustment of step 1304 by adjusting the voltage applied to the static charge control electrode 1112. An image of the reflecting member 1109 is utilized as the image acquired in the mirror state. The reflecting member is a metallic member installed along the optical axis and formed with an opening for passing the primary electron beam. When the charged particles returned back in the mirror state strike the bottom surface of the reflecting member, the secondary charged particle detector 1105 detects an image where the opening forms a shadow. The SEM type inspection device of this embodiment can estimate the amount of localized static charge at the primary electron beam irradiation position by finding the amount of deviation in this shadow. The amount of deviation may also be calculated by using a specified evaluation point formed on the sample or an image of another structural component in the electron optical system the same as in the first embodiment.

Step 1305 is a step for magnifying the image detected in step 1304, the same as in the device of the first embodiment.

The static charge voltage calculation step 1306 is executed when the magnification adjustment ends. In this step, a primary electron beam is irradiated onto the sample set in the mirror state and a mirror electron image of the reflecting member 1109 is acquired. This acquired mirror image is compared with the mirror image of a sample with no static charge contained in the spare data called up in step 1204 of FIG. 12, and the amount of deviation in the image then calculated. The amount of deviation in the actual image and the reference image are calculated, and compared with the calibration curve for the deviation amount minus the retarding voltage, using the same steps as in FIG. 10A. Moreover, the differential amount $V_r'-V_r$ of the retarding voltage $V_r$ and the surface voltage of the sample are calculated, and local static charge voltage for the measurement points is calculated.

Next in step 1307, the calculated localized static charge voltage is compared with the target static charge control value at each point on the sample, and the voltage to apply to the static control electrode (actually the differential in amounts of the retarding voltage and voltage applied to the static control electrodes), and the flood gun output (the irradiating energy of the electron beam, controllable by the flood beam accelerating voltage) are set. The flood gun control amount and the voltage applied to the static charge control electrodes that were set are stored in information processor device 1119 as the data table. The astigmatism compensation amount, primary electron beam alignment compensation amount, and objective lens compensation amount may as usual be calculated, and incorporated into data for the focus map in this step. In step 1380, a decision step is performed to decide whether or not there is a next evaluation position. The focus map and the static charge control map are generated from hereon by repeating the loop in 1303-1308.

The inspection image acquisition step 1309 is executed when the focus map and static control maps are generated. In the actual operation, a stage movement step equivalent to step 1206 in FIG. 12 is interposed between the step 1308 and step 1309 however this is omitted in FIG. 13.

When the stage movement ends, a decision step is made to decide whether static charge control processing is needed or not. The static charge voltage may have already reached a value equivalent to the target value according to the wafer position. If static charge control processing is needed then the static charge control processing step 1311 is performed and the focus map and static charge control map stored in the information processor device 1119 are searched. The information processor device 1119 conveys the searched data to the electron optical control device 1120, and then each control power supply supplies a specified voltage to the flood gun 1111 and the static charge control electrode 1112.

When static charge control by flood beam irradiation is complete, the primary electron beam is irradiated onto the sample in step 1312, and the secondary charged particle image signal is detected. This detected secondary charged particle image signal is forwarded by way of the preamp 1106 to the information processing device 1119. The information processing device 1119 synchronizes the forwarded detected signal with the scanning deflector signal of scanning deflector 1107, and generates image data within a specified scanning range. The generated image data is further forwarded to the image processor unit 1125 and pixels inspected by comparison processing. If inspection results reveal a defect then coordinate information for the applicable inspection point is stored in the storage unit within the image processor unit 1125. This step is the same as step 1212 in FIG. 12, and continues to step 1213 of FIG. 12. The process from step 1213 onward is the same as already described for FIG. 12 so a description is omitted here.

The device of this embodiment renders an SEM type external inspection device having a high defect detection rate that also causes extremely little damage to the sample from electron beam irradiation. The SEM type external inspection device of the related art measured the static charge voltage on the sample surface by using a surface voltmeter positioned in the sample replacement chamber or at the aligner position and therefore could only acquired a static charge voltage map or a focus map of the causes of the global static charge. There was therefore no detection technique for cases such as when the sample surface voltage at specified points on the sample, deviated greatly from the local static charge predicted from the global static charge. The sample inspection therefore had to be performed under conditions different from the target (desired) static charge voltage and consequently the defect capture rate was low, and there was a large quantity of false or unreliable information.

The device of this embodiment renders an SEM type external inspection device capable of measuring the localized static charge voltage without any effects on the surface voltage of the sample, and therefore can set a static charge control value that matches the surface voltage of the actual sample. The SEM type external inspection device therefore has a high defect capture rate and causes extremely little damage to the sample. The structure of the device of this embodiment moreover the same as the first embodiment is not limited to SEM type external inspection devices and needless to say, is applicable to charged particle beam device where problems from static charges are likely to occur.

What is claimed is:

1. A charged particle beam device including:
    an electron optical system to irradiate a sample with a primary charged particle beam and detect and output secondary charged particles as a signal output, and
    a controller that regulates a voltage applied to the applicable electron optical system and the sample,
    wherein the controller comprises a computer readable medium containing instructions that, when executed, cause the charged particle beam device to form a first image of a non-charged sample as a reference image in a state where a voltage applied to the sample that is higher than an accelerated energy of the primary charged particle beam, form a second image of a charged sample as an object of inspection in a state where the voltage applied to the sample is higher than the accelerated energy of the primary charged particle beam, and calculate a static charge of a surface of the charged sample based on a differential between the first and the second images, and
    wherein the controller controls the electron optical system based on the static charge of the surface of the charged sample.

2. A charged particle beam device according to claim 1, wherein the electron optical system contains an astigmatism compensator, and wherein the electron optical system controls the applicable astigmatism compensator based on the differential between the first and the second images.

3. A charged particle beam device according to claim 1, wherein the electron optical system includes an adjusting unit that adjusts an optical axis of the primary charged particle beam, and wherein the electron optical system controls the applicable optical axis adjusting unit based on the differential between the first and the second images.

4. A charged particle beam device according to claim 1, wherein the electron optical system includes an objective lens, and wherein the electron optical system controls the applicable objective lens based on the differential between the first and the second images.

5. A charged particle beam device according to claim 1, further comprising: a second charged particle beam irradiating unit that irradiates a charged particle beam for controlling the static charge at a charged particle beam irradiation position,
    wherein the electron optical system contains a static charge control electrode, and
    wherein the electron optical system controls the second charged particle beam irradiation unit and the voltage applied to the static charge control electrode based on the differential between the first and the second images.

6. A charged particle beam device according to claim 1, further comprising: an astigmatism compensator, an adjusting unit that adjusts an optical axis of the primary charged particle beam, an objective lens, a second charged particle beam irradiating unit that irradiates a charged particle beam for controlling the static charge at a charged particle beam irradiation position, and an information processing device,
    wherein the information processing device stores a data table for storing control parameter values for the astigmatism compensator, the adjusting unit, the objective lens, and the second charged particle beam irradiating unit in association with the differential between the first and the second images.

7. A charged particle beam device according to claim 1, wherein the controller forms projected images of the sample as the first and second images.

8. A charged particle beam device according to claim 5, wherein the controller generates data that controls parameter values for the static charge control electrode and the second charged particle beam irradiating unit that are linked with position on the sample surface, and wherein the controller controls the sample surface voltage at the primary charged particle beam irradiation position by utilizing the data.

* * * * *